(12) United States Patent
Wang et al.

(10) Patent No.: US 9,272,134 B2
(45) Date of Patent: *Mar. 1, 2016

(54) PACEMAKERS AND PACEMAKER ELECTRODES

(75) Inventors: Yu-Quan Wang, Beijing (CN); Li Fan, Beijing (CN); Wen-Mei Zhao, Beijing (CN); Li Qian, Beijing (CN); Chen Feng, Beijing (CN); Liang Liu, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/477,259

(22) Filed: May 22, 2012

(65) Prior Publication Data

US 2013/0158643 A1 Jun. 20, 2013

(30) Foreign Application Priority Data

Dec. 15, 2011 (CN) .......................... 2011 1 0420293

(51) Int. Cl.
*A61N 1/05* (2006.01)
*B82Y 5/00* (2011.01)
*A61N 1/375* (2006.01)
*A61N 1/362* (2006.01)

(52) U.S. Cl.
CPC .............. *A61N 1/056* (2013.01); *A61N 1/0565* (2013.01); *A61N 1/0573* (2013.01); *A61N 1/362* (2013.01); *A61N 1/375* (2013.01); *B82Y 5/00* (2013.01)

(58) Field of Classification Search
USPC ........................................................ 600/372
See application file for complete search history.

(56) References Cited

U.S. PATENT DOCUMENTS

| | | | |
|---|---|---|---|
| 7,596,415 B2 | 9/2009 | Brabec et al. | |
| 7,673,521 B2 * | 3/2010 | Ajayan et al. | 73/774 |
| 8,048,256 B2 | 11/2011 | Feng et al. | |
| 2006/0272701 A1 * | 12/2006 | Ajayan et al. | 136/263 |
| 2007/0060815 A1 * | 3/2007 | Martin et al. | 600/372 |
| 2009/0194313 A1 | 8/2009 | Jiang et al. | |
| 2010/0147829 A1 | 6/2010 | Liu et al. | |
| 2012/0053649 A1 | 3/2012 | Liu et al. | |
| 2012/0107591 A1 | 5/2012 | Wang et al. | |
| 2013/0158644 A1 * | 6/2013 | Qian et al. | 607/119 |

FOREIGN PATENT DOCUMENTS

| | | |
|---|---|---|
| CN | 201616285 | 10/2010 |
| CN | 101927057 | 12/2010 |
| CN | 102061101 | 5/2011 |
| TW | 201039670 | 11/2010 |
| TW | I345792 | 7/2011 |

* cited by examiner

*Primary Examiner* — Carl H Layno
*Assistant Examiner* — Jon Eric C Morales
(74) *Attorney, Agent, or Firm* — Novak Druce Connolly Bove + Quigg LLP

(57) ABSTRACT

A pacemaker includes an electrode line having a lead and an electrode. The electrode includes a carbon nanotube composite structure having a matrix and a carbon nanotube structure located in the matrix. The matrix comprises a first surface and a second surface substantially perpendicular to the first surface. The carbon nanotube structure includes a first end electrically connect to the lead. The carbon nanotube structure is substantially parallel to the second surface of the matrix. A distance between the carbon nanotube structure and the second surface of the matrix is less than 10 micrometers.

19 Claims, 11 Drawing Sheets

PACEMAKERS AND PACEMAKER ELECTRODES

CROSS-REFERENCE TO RELATED APPLICATIONS

This application claims all benefits accruing under 35 U.S.C. §119 from China Patent Application No. 201110420293.5, filed on Dec. 15, 2011 in the China Intellectual Property Office, the disclosure of which is incorporated herein by reference. This application is related to applications entitled, "PACEMAKERS AND PACEMAKER ELECTRODES", filed May 22, 2012 Ser. No. 13/477,261.

BACKGROUND

1. Technical Field

The present application is related to pacemakers and pacemaker electrodes, and more particularly to pacemakers and pacemaker electrodes using carbon nanotubes.

2. Description of Related Art

Pacemakers are electrical therapy apparatuses which can be implanted into an organ or a tissue of human beings to treat the organ or the tissue. The pacemaker includes power, a pulse generator and an electrode line. An electrical pulse signal can be generated by the pulse generator through the electrode line to stimulate the organ or tissue. Thus, dysfunctions of the organ or the tissue of human beings can be treated.

However, an electrode in the electrode line is made of metal or alloy and the electrode has a small diameter, so the mechanical strength and toughness of the electrode is relatively low.

What is needed, therefore, is to provide a pacemaker and a pacemaker electrode, which can overcome the above-described shortcomings.

BRIEF DESCRIPTION OF THE DRAWINGS

Many aspects of the embodiments can be better understood with reference to the following drawings. The components in the drawings are not necessarily to scale, the emphasis instead being placed upon clearly illustrating the principles of the present disclosure. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
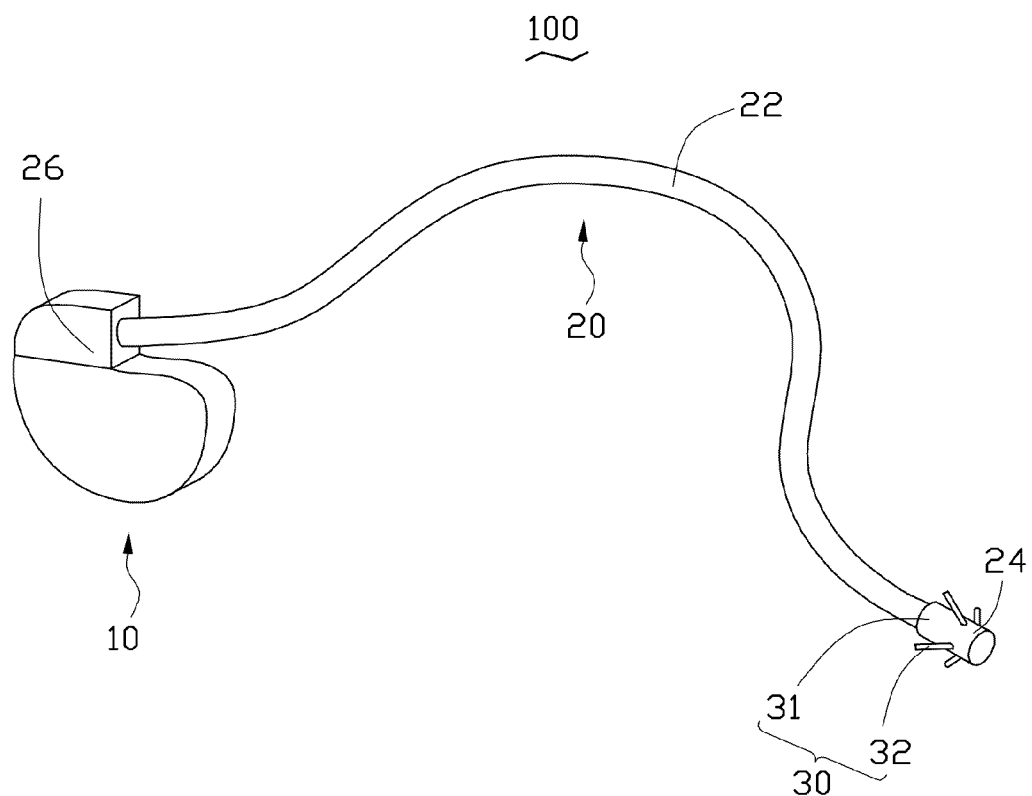
FIG. 1 shows an isometric view of one embodiment of a pacemaker.

Referring to FIG. 1, a pacemaker 100 of one embodiment is provided. The pacemaker 100 can be a brain pacemaker or a cardiac pacemaker. The pacemaker 100 is a unipolar pacemaker. The pacemaker 100 includes a pulse generator 10 and an electrode line 20 electrically connected to the pulse generator 10. The pulse generator 10 can generate electrical pulse signals traveling through the electrode line 20 to stimulate the brain tissue or the heart tissue.

The pulse generator 10 includes a shell (not shown), a power source (not shown), a pulse generating circuit (not shown), a control circuit (not shown) and at least one interface (not shown). The power source, the pulse generating circuit and the control circuit are packaged in the shell. A positive electrode of the power source is electrically connected to the shell. The power source can power the pulse generating circuit and the control circuit. The pulse generating circuit can generate the electrical pulse signals. The control circuit can control the pulse generating circuit to generate the electrical pulse signals. The shell can be made of metals or alloys having bio-compatibility and corrosion resistance characteristics to protect internal components. In one embodiment, the shell is made of titanium.

The electrode line 20 includes a lead 22, an electrode 24, and an interface 26. The interface 26 and the electrode 24 are located at different ends of the lead 22. The lead 22 has good conductivity and is used to transmit the electrical pulse signals from the pulse generator 10 to the electrode 24. The electrode 24 is electrically connected to the lead 22 and is used to contact with the brain tissue or the heart tissue. The interface 26 matches the at least one interface of the pulse generator 10 and is used to electrically connect the electrode line 20 to the pulse generator 10. The lead 22 can be a linear structure or a helical structure. A diameter of the helical structure can be in a range from about 4 millimeters to about 6 millimeters. In one embodiment, the diameter of the helical structure is about 5 millimeters. A thread pitch of the helical structure can be in a range from about 0 millimeter to about 10 millimeters.

Figure 2:
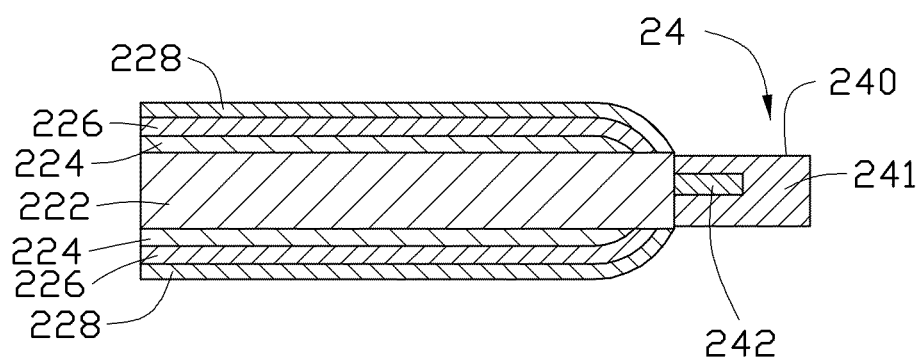
FIG. 2 shows a schematic view of one embodiment of an electrode line in the pacemaker of FIG. 1.

Referring to FIG. 2, the lead 22 includes a first conductor 222, an insulation layer 224, a shielding layer 226, and a sheath 228 arranged from inside to outside. The insulation layer 224 is located on an outer surface of the first conductor 222 to insulate the first conductor 222 from the shielding layer 226. In one embodiment, the lead 22 includes more than one first conductor 222 and more than one insulation layer 224, with each insulation layer 224 located on an outer surface of each first conductor 222 to insulate the first conductors 222 from each other. The sheath 228 is located on an outer surface of the shielding layer 226 to protect the lead 22.

A material of the first conductor 222 can be MP35N® (a registered trademark of SPS Technologies Inc.), 35NLT® (a registered trademark of Fort Wayne Metals Research Products Corp), steel, carbon fiber, carbon nanotubes, tantalum, titanium, zirconium, niobium, titanium alloy, copper, silver, platinum, titanium-yttrium alloy, titanium-palladium alloy, or other metals. In one embodiment, the first conductor 222 is a copper wire.

The insulation layer 224 can be located on an outer surface of the first conductor 222 to form a tube structure. The insulation layer 224 is used to insulate the first conductor 222 from the outer environment. A material of the insulation layer 224 can be any suitable insulative material, such as polytetrafluoroethylene, polyethylene, polypropylene, polystyrene, polyethylene foam and nano-clay-polymer composite material. In one embodiment, the material of the insulation layer 224 is polytetrafluoroethylene.

The shielding layer 226 can be located on an outer surface of the insulation layer 224 and can be used to shield electromagnetic signals or external signals. In one embodiment, the shielding layer 226 can be formed by weaving conductive wires or by winding conductive films around the insulating layer 244. The wires can be metal wires, carbon nanotube wires or composite wires having carbon nanotubes. The films can be metal films, carbon nanotube films, or composite films having carbon nanotubes.

The sheath 228 can be located on an outer surface of the shielding layer 226 and can be used to prevent the lead 22 from machinery damage and chemical exposure damage, for example. A material of the sheath 228 can be a biocompatible and corrosion resistant polymer material. The material of the sheath 228 can be polyurethane or silicone rubber. In one embodiment, the material of the sheath 228 is polyurethane.

The electrode 24 can be electrically connected to the first conductor 222 with a conductive glue. The electrode 24 can include a carbon nanotube composite structure. The carbon nanotube composite structure can be formed by at least one carbon nanotube structure 242 and a matrix 241. The at least one carbon nanotube structure 242 can have a first end and a second end opposite to the first end. The matrix 241 can have a first surface and at least one second surface 240 substantially perpendicular to the first surface. The at least one carbon nanotube structure 242 can be located in the matrix 241. Specifically, the at least one carbon nanotube structure 242 can be substantially parallel to the at least one second surface 240 of the matrix 241 and the first end of the at least one carbon nanotube structure 242 can be located in the matrix 241. A distance between the at least one carbon nanotube structure 242 and the at least one second surface 240 of the matrix 241 can be less than 10 micrometers. In some embodiments, the distance between the at least one carbon nanotube structure 242 and the at least one second surface 240 of the matrix 241 is less than 100 nanometers. In other embodiments, the distance between the at least one carbon nanotube structure 242 and the at least one second surface 240 of the matrix 241 is less than 30 nanometers. The at least one second surface 240 of the matrix 241 can be used to contact and stimulate the brain tissue or the heart tissue. The second end of the at least one carbon nanotube structure 242 can protrude out of the first surface of the matrix 241 and electrically connect to the first conductor 222 by a conductive glue. The carbon nanotube composite structure has good conductivity if the distance between the at least one carbon nanotube structure 242 and the at least one second surface 240 of the matrix 241 is less than 10 micrometers. The electrode 24 can further have a third surface opposite to the first surface. The third surface is substantially perpendicular to at least one second surface 240. In some embodiments, a distance between the first end of the at least one carbon nanotube structure 242 and the third surface 240 of the matrix 241 is less than 10 micrometers, thus, the third surface of the matrix 241 can also be used to contact and stimulate the brain tissue or the heart tissue.

Each carbon nanotube structure 242 can include a number of carbon nanotubes. The carbon nanotubes in the at least one carbon nanotube structure 242 can be combined firmly by van der Waals attractive force to form a free-standing structure. The term 'free-standing' includes structures that do not have to be supported by a substrate. Adjacent carbon nanotubes of the at least one carbon nanotube structure 242 can be combined by van der Waals attractive force to form a number of interspaces. Width of the interspaces can be in a range from about 1 nanometer to about 450 nanometers. The matrix 241 can be located in the interspaces of the at least one carbon nanotube structure 242.

A material of the matrix 241 can be epoxy resin, bismaleimide resin, cyanate ester resins, polypropylene, polyethylene, polystyrene, polyvinyl alcohol, polyphenylene enol, polycarbonate, poly methyl methacrylate, or other polymers.

The at least one carbon nanotube structure 242 can be formed by at least one carbon nanotube film or at least one carbon nanotube wire. The at least one carbon nanotube film can be drawn carbon nanotube films, pressed carbon nanotube films or flocculated carbon nanotube films. The at least one carbon nanotube wire can be twisted carbon nanotube wires or non-twisted carbon nanotube wires.

Figure 3:
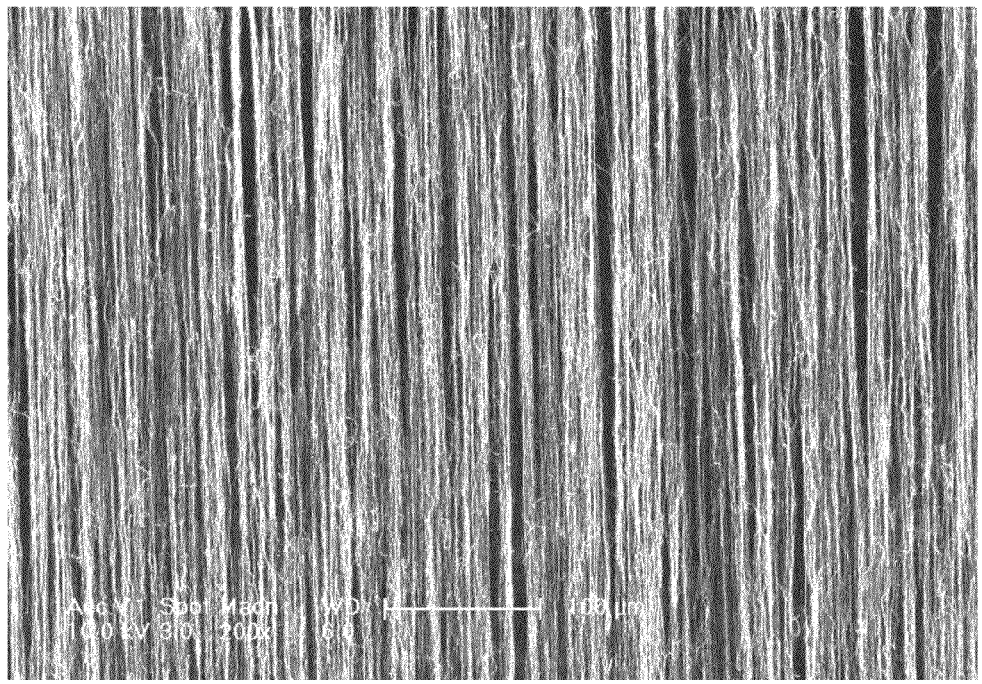
FIG. 3 is a Scanning Electron Microscope (SEM) image of a drawn carbon nanotube film.

Referring to FIG. 3, the drawn carbon nanotube film includes a number of carbon nanotubes that are arranged substantially parallel to a surface of the drawn carbon nanotube film. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals force, to form a free-standing film. A small number of the carbon nanotubes are randomly arranged in the drawn carbon nanotube film, and has a small if not negligible effect on the larger number of the carbon nanotubes in the drawn carbon nanotube film arranged substantially along the same direction. Some variation can occur in the orientation of the carbon nanotubes in the drawn carbon nanotube film. Microscopically, the carbon nanotubes oriented substantially along the same direction may not be perfectly aligned in a straight line, and some curve portions may exist. Contact between some carbon nanotubes located substantially side by side and oriented along the same direction cannot be totally excluded. Interspaces are defined in the drawn carbon nanotube film by adjacent carbon nanotubes.

More specifically, the drawn carbon nanotube film can include a number of successively oriented carbon nanotube segments joined end-to-end by van der Waals force therebetween. Each carbon nanotube segment includes a number of carbon nanotubes substantially parallel to each other, and joined by van der Waals force therebetween. The carbon nanotube segments can vary in width, thickness, uniformity, and shape. The carbon nanotubes in the drawn carbon nanotube film are also substantially oriented along a preferred orientation. The width of the drawn carbon nanotube film relates to the carbon nanotube array from which the drawn carbon nanotube film is drawn.

The drawn carbon nanotube film can be drawn from a carbon nanotube array. The method for drawing the drawn carbon nanotube film includes: providing the carbon nanotube array capable of having a film drawn therefrom; and pulling/drawing out the drawn carbon nanotube film from the carbon nanotube array. Adhesive tape, pliers, tweezers, or another tool allowing multiple carbon nanotubes to be gripped and pulled simultaneously can be used to pull/draw out the carbon nanotube film.

The carbon nanotube array can be formed by a chemical vapor deposition (CVD) method. The carbon nanotube array includes a number of carbon nanotubes substantially parallel to each other and approximately perpendicular to the substrate. The carbon nanotubes in the carbon nanotube array are closely packed together by van der Waals force. The carbon nanotubes in the carbon nanotube array can be single-walled carbon nanotubes, double-walled carbon nanotubes, multi-walled carbon nanotubes, or combinations thereof. The diameter of the carbon nanotubes can be in the range from about 0.5 nanometers to about 50 nanometers. The height of the carbon nanotubes can be in the range from about 50 nanometers to 5 millimeters. In one embodiment, the height of the carbon nanotubes can be in a range from about 100 microns to 900 microns.

The drawn carbon nanotube film can be pulled/drawn by the following sub-steps: selecting a carbon nanotube segment having a predetermined width from the carbon nanotube array; and pulling the carbon nanotube segment at an even/uniform speed to achieve a uniform drawn carbon nanotube film. More specifically, during the pulling process, as the initial carbon nanotube segment is drawn out, other carbon nanotube segments are also drawn out end-to-end due to the van der Waals force between the ends of the adjacent segments. This process of drawing ensures that a continuous, uniform drawn carbon nanotube film having a predetermined width can be formed.

Figure 4:
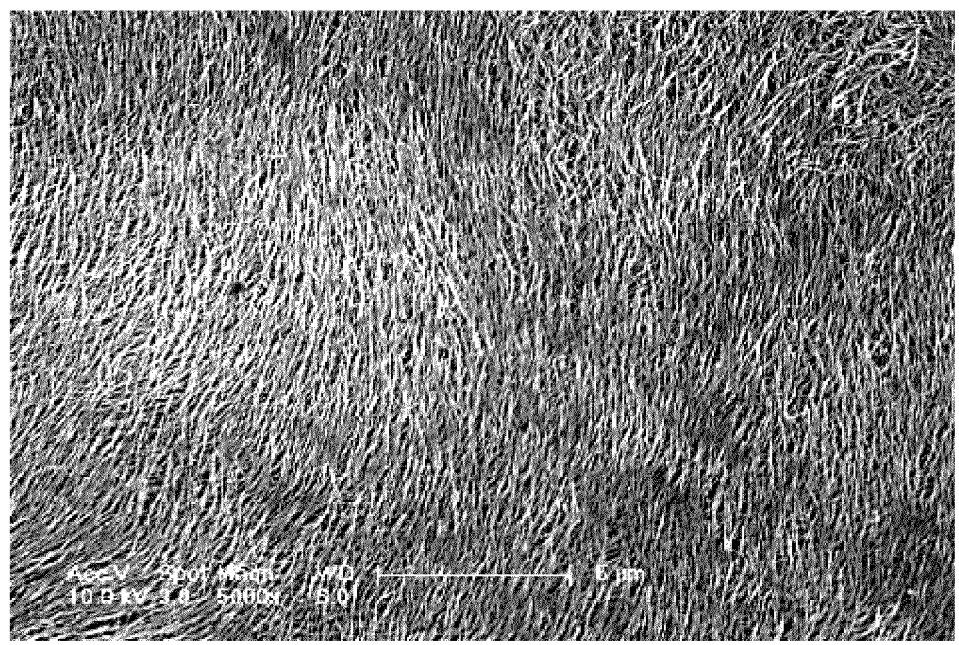
FIG. 4 is an SEM image of a pressed carbon nanotube film.

The pressed carbon nanotube films can be formed by pressing a carbon nanotube array down on a substrate. Referring to FIG. 4, the carbon nanotubes in the pressed carbon nanotube array are arranged along a same direction or along different directions. The carbon nanotubes in the pressed carbon nanotube array can rest upon each other. Adjacent carbon nanotubes are attracted to each other and combined by van der Waals force to form a number of interspaces. Width of the interspaces can be in a range form about 1 nanometer to about 450 nanometers. An angle between a primary alignment direction of the carbon nanotubes and a surface of the pressed carbon nanotube array is about 0 degrees to about 15 degrees. The greater the pressure applied, the smaller the angle obtained. If the carbon nanotubes in the pressed carbon nanotube array are arranged along different directions, the carbon nanotube structure can be isotropic. The thickness of the pressed carbon nanotube array can range from about 0.5 nm to about 1 millimeter. The length of the carbon nanotubes can be larger than 50 micrometers.

Figure 5:
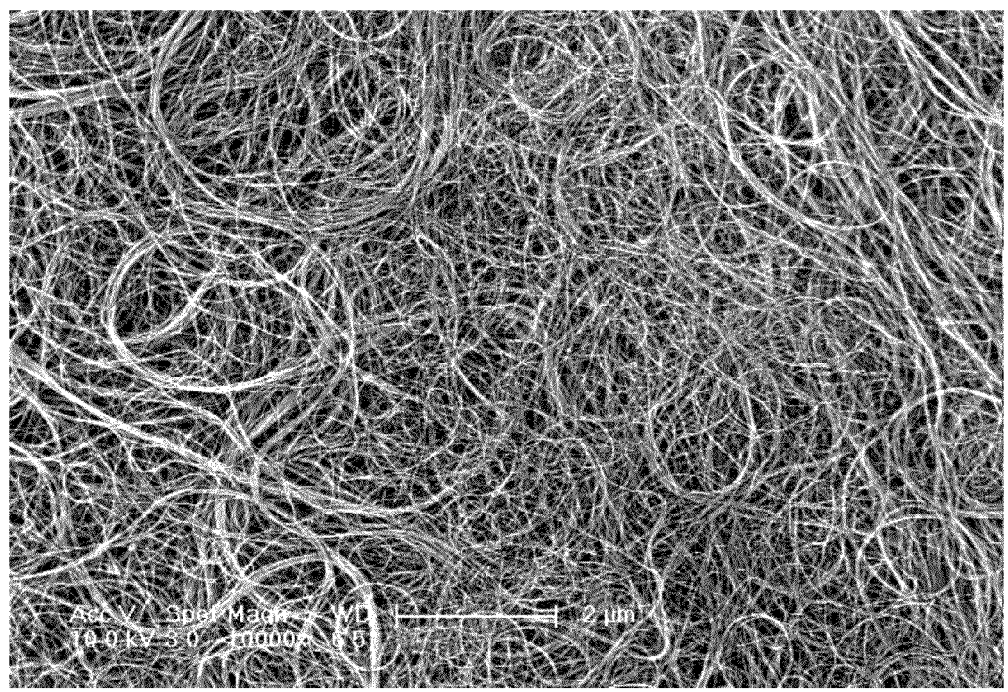
FIG. 5 is an SEM image of a flocculated carbon nanotube film.

The flocculated carbon nanotube film can be formed by a flocculating method. Referring to FIG. 5, the flocculated carbon nanotube film can include a number of long, curved, disordered carbon nanotubes entangled with each other. A length of the carbon nanotubes can be greater than 10 centimeters. Further, the flocculated carbon nanotube film can be isotropic. Here, "isotropic" means the carbon nanotube film has properties approximately identical in all directions substantially parallel to a surface of the carbon nanotube film. The carbon nanotubes can be substantially uniformly distributed in the carbon nanotube film. A thickness of the flocculated carbon nanotube film can range from about 1 micrometer to about 1 millimeter.

Figure 6:
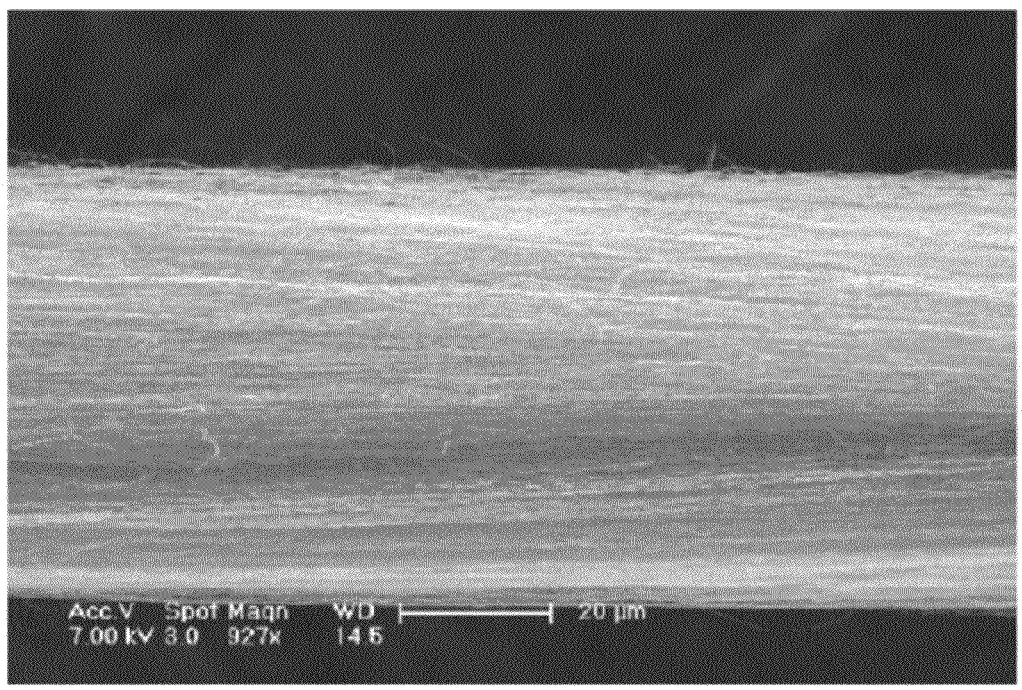
FIG. 6 is an SEM image of a twisted carbon nanotube wire.

Referring to FIG. 6, the twisted carbon nanotube wire includes a number of carbon nanotubes oriented around an axis of the twisted carbon nanotube wire. The carbon nanotubes are aligned around the axis of the carbon nanotube twisted wire like a helix. More specifically, the twisted carbon nanotube wire includes a number of successive carbon nanotubes joined end to end by van der Waals attractive force therebetween. Adjacent carbon nanotubes are combined by van der Waals attractive force therebetween to form a number of interspaces. A length and a diameter of the twisted carbon nanotube wire can be arbitrarily set as desired. The twisted carbon nanotube wire can be formed using a mechanical force to turn two ends of the drawn carbon nanotube film in opposite directions.

Figure 7:
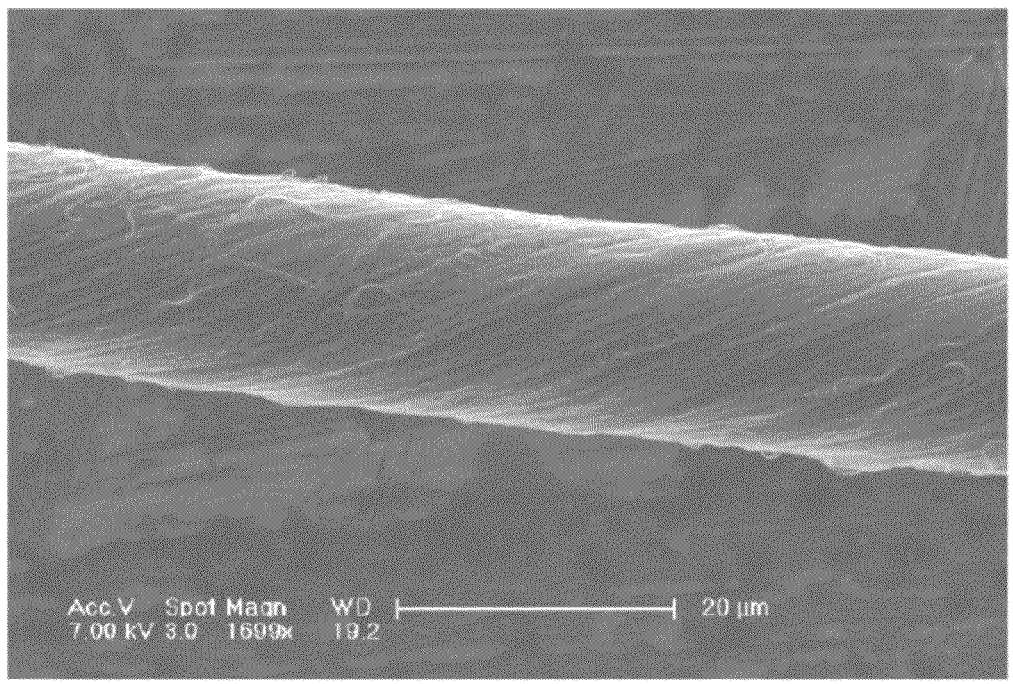
FIG. 7 is an SEM image of a non-twisted carbon nanotube wire.

Referring to FIG. 7, the non-twisted carbon nanotube wire includes a number of carbon nanotubes substantially oriented along a same direction (i.e., a direction along the length of the non-twisted carbon nanotube wire). The carbon nanotubes are substantially parallel to the axis of the non-twisted carbon nanotube wire. Specifically, the non-twisted carbon nanotube wire includes a number of successive carbon nanotube segments joined end to end by van der Waals attractive force therebetween. Each carbon nanotube segment includes a number of carbon nanotubes substantially parallel to each other, and combined by van der Waals attractive force therebetween.

The non-twisted carbon nanotube wire can be formed by treating the drawn carbon nanotube film with an organic solvent. Specifically, the drawn carbon nanotube film is treated by applying the organic solvent to the drawn carbon nanotube film and soaking the entire surface of the carbon nanotube film. After being soaked by the organic solvent, the adjacent paralleled carbon nanotubes in the drawn carbon nanotube film will bundle together, due to the surface tension of the organic solvent when the organic solvent volatilizes. Thus, the drawn carbon nanotube film will be shrunk into non-twisted carbon nanotube wire. The organic solvent is volatile.

In one embodiment, the carbon nanotube composite structure includes a carbon nanotube structure 242. The carbon nanotube structure 242 includes a number of drawn carbon nanotube films stacked with each other, and the carbon nanotubes in the carbon nanotube structures 242 are oriented substantially along a same direction perpendicular to the first surface of the matrix 241. The carbon nanotubes are joined end to end by van der Waals force therebetween along the oriented direction.

A fixing member 30 can be further fixed on an outer surface of the sheath 228 adjacent to the electrode 24. The fixing member 30 can also be made of a high polymer material like polyurethane or silicone rubber. The fixing member 30 can include a fixing ring 31 and a number of fixing wings 32. The fixing ring 31 can have a cylindrical structure. The fixing wings 32 can have a claviform structure extending along a direction from an outer surface of the fixing ring 31 to an axis of the fixing ring 31. An angle between the axis of the claviform structure and the axis of the fixing ring 31 can be in a range from about 30 degrees to about 60 degrees. The fixing wing 264 can be wrapped with human tissue after the fixing member 30 is implanted into the human body to fix the electrode 24 in place.

In use, the electrode line 20 is implanted into the body, and the electrode 24 is fixed to a chosen tissue by the fixing member 30. The electrical pulse signals can be generated by the pulse generating circuit and transported to the electrode 24 by the first conductor 222 to stimulate and treat the chosen tissue. Furthermore, an electric potential difference between the shell and the electrode 24 can be obtained by the pulse generator 10, thus a frequency and an intensity of the electrical pulse signals can be adjusted according to the electric potential difference.

A method for making the carbon nanotube composite structure includes the following steps:

(a) providing a matrix 241 having a surface and a carbon nanotube structure 242 including a number of carbon nanotubes and a number of interspaces;

(b) placing the carbon nanotube structure 242 on the surface of the matrix 241; and (c) exposing the carbon nanotube structure 242 and the matrix 241 to electromagnetic waves.

In step (a) and (b), the matrix can be made of epoxy resin, bismaleimide resin, cyanate ester resins, polypropylene, polyethylene, polystyrene, polyvinyl alcohol, polyphenylene enol, polycarbonate, poly methyl methacrylate, or other polymers. The shape of the matrix is not limited. In one embodiment, the matrix is a cuboid made of polyethylene.

The carbon nanotubes in the carbon nanotube structure 242 can be combined firmly by van der Waals attractive force therebetween to form a free-standing structure. The term 'free-standing' includes structures that do not have to be supported by a substrate. Adjacent carbon nanotubes in the carbon nanotube structure 242 can be combined by van der Waals attractive force therebetween to form the interspaces. Width of the interspaces can be in a range from about 1 nanometer to about 450 nanometers. In one embodiment, the carbon nanotube structure 242 is a drawn carbon nanotube film. The carbon nanotube structure 242 is disposed on the surface of the matrix 241.

In step (c), a power of the electromagnetic waves can be in a range from about 300 W to about 2000 W. The power of the electromagnetic wave is determined by the melting point of the materials of the matrix 241. The higher the melting points of the materials, the higher the power of the electromagnetic wave. The electromagnetic wave can be radio frequency, microwave, near infrared, or far infrared. In one embodiment, the electromagnetic waves are microwaves. A power of the microwaves can be in a range from about 300 W to about 1500 W. A frequency of the microwaves can be in a range from about 1 GHz to about 10 GHz. The carbon nanotube structure 242 and the matrix 241 are kept and heated in the chamber filled with microwaves for about 1 second to about 300 seconds. In other embodiments, the carbon nanotube structure 242 and the matrix 241 are kept and heated in the chamber filled with microwaves about 3 seconds to about 90 seconds. In one embodiment, the time is about 30 seconds.

Figure 8:
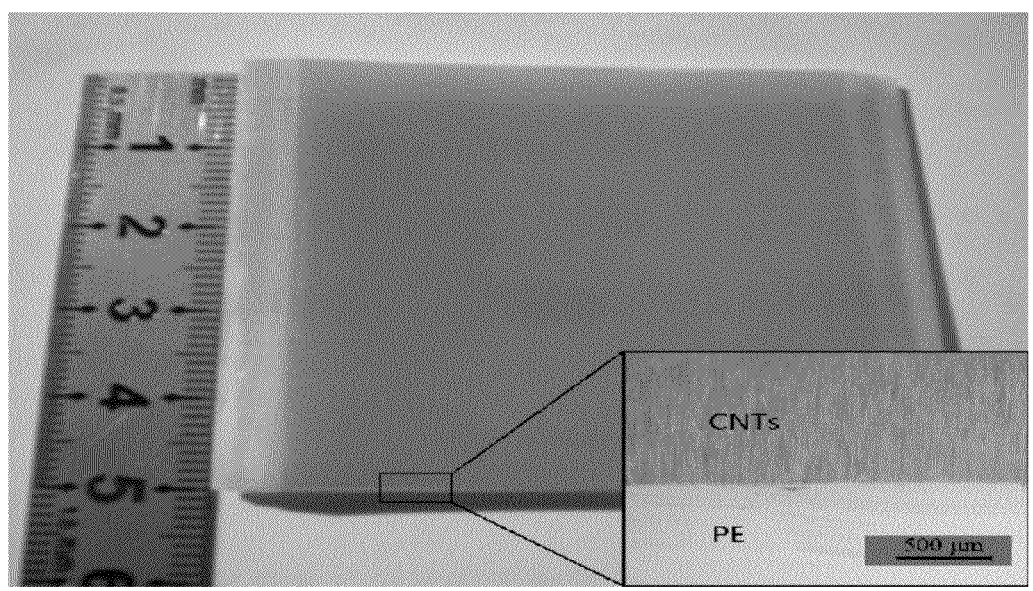
FIG. 8 is an SEM image and a picture of a carbon nanotube composite structure in the pacemaker of FIG. 1.
Figure 9:
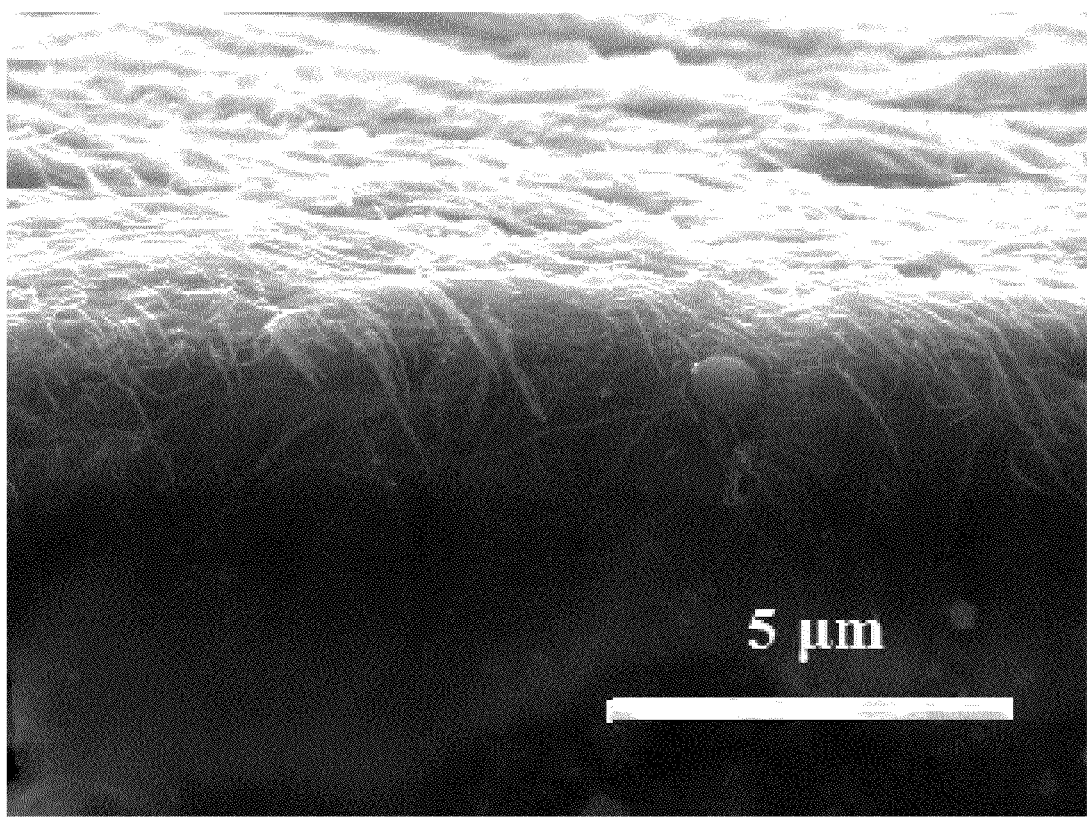
FIG. 9 is an SEM image of the profile of the carbon nanotube composite structure in the pacemaker of FIG. 8.

The carbon nanotube structure 242 is exposed in the electromagnetic waves until a portion of the matrix 241 is melted and permeates into interspaces of the carbon nanotube structure 242. In one embodiment, the carbon nanotube structure 242 is located on the surface of the matrix 241 and can be placed into a chamber filled with electromagnetic waves. The material of the matrix 241 is a polymer which absorbs very little electromagnetic wave energy. As such, the matrix 241 will not be heated by the electromagnetic waves. The carbon nanotube structure 242 is located on the surface of the matrix 241 and can absorb the energy of the microwaves and generate heat. Because the carbon nanotube structure 242 has a small heat capacity per unit area, a temperature of the carbon nanotube structure 242 rises quickly. This temperature increase will heat the surface of the matrix 241 until the carbon nanotube structure 242 is able to infiltrate the matrix 241. In one embodiment, the surface of the matrix 241 is melted by the heat, and liquid matrix 241 is present on the surface. Because the wettability of the liquid matrix 241 and the carbon nanotube structure 242 is good, the liquid matrix 241 will infiltrate into the interspaces of the carbon nanotube structure 242, thereby coating the carbon nanotube structure 242 with the liquid matrix 241. After the liquid matrix 241 wets the whole carbon nanotube structure 242, the material of the matrix 241 will stop moving into the interspaces and will be full of the matrix 241 material. In other words, the carbon nanotube structure 242 settles into the matrix 241, below the surface of the matrix 241. Referring to FIG. 8 and FIG. 9, a distance between the surface of the matrix 241 and the carbon nanotube structure 242 is less than 10 micrometers. Namely, a thickness of part of the matrix 241 above the carbon nanotube structure 242 is less than 10 micrometers. The heat generated by the carbon nanotube structure 242 can be absorbed by the surface of the matrix 241, and the temperature of the carbon nanotube structure 242 can be controlled under 700° C., and the carbon nanotube structure 242 will not burn.

In one embodiment, the matrix 241 is made of polyethylene, which has a melting point of about 137° C. The carbon nanotube structure 242 and the matrix 241 can be kept in the chamber filled with microwaves until the temperature of the surface reaches slightly above the melting point of about 137° C. The carbon nanotube structure 242 and the matrix 241 can be kept in the chamber for about 10 seconds, and the carbon nanotube structure 242 will embed in the matrix 241.

Step (c) can be carried out in a vacuum environment of about $10^{-2}$ Pascals to about $10^{-6}$ Pascals, or in a specific atmosphere of protective gases including nitrogen gas and inert gases. The carbon nanotube structure 242 can generate a lot of heat and reach the temperature of about 2000° C. to embed into the matrix 241, which can have a higher melting point when the carbon nanotube structure 242 operates in a vacuum environment or in a specific atmosphere.

Figure 10:
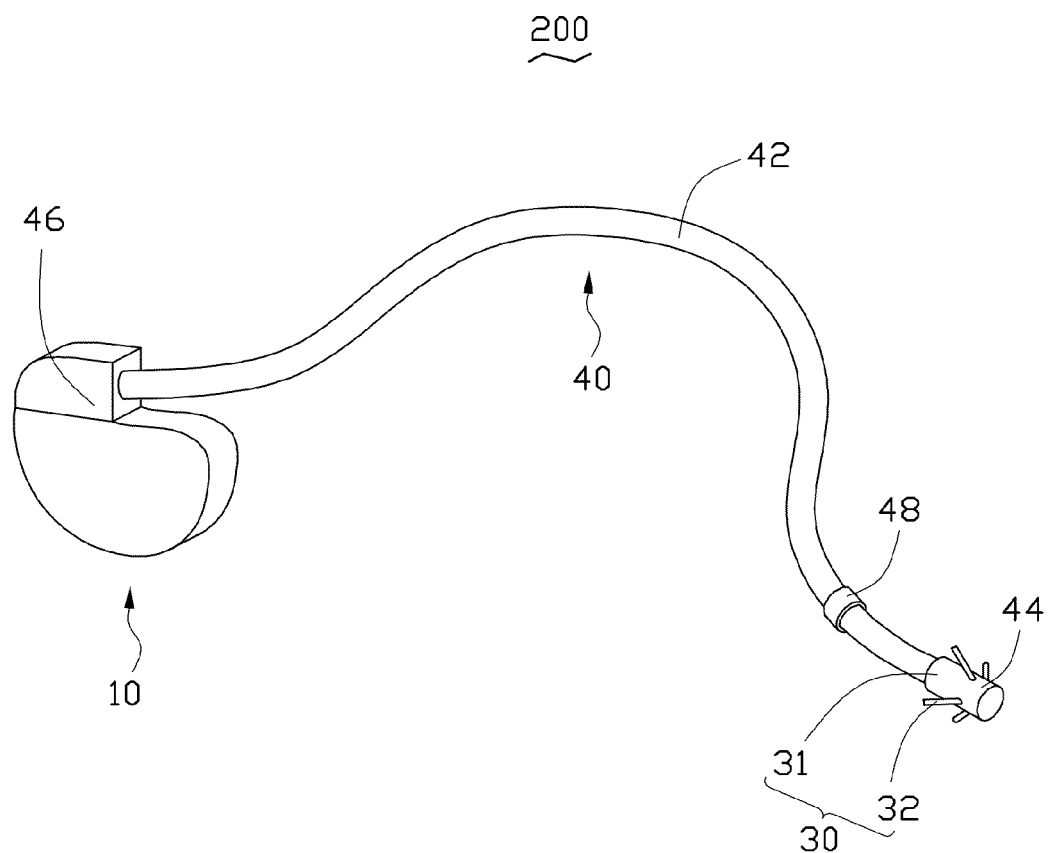
FIG. 10 shows an isometric view of another embodiment of a pacemaker.

Referring to FIG. 10, another embodiment of a pacemaker 200 is provided. The pacemaker 100 is a bipolar pacemaker. The pacemaker 100 includes a pulse generator 10 and an electrode line 40 electrically connected to the pulse generator 10. The pulse generator 10 can generate electrical pulse signals traveling through the electrode line 40 to stimulate the brain tissue or the heart tissue.

The pulse generator 10 of the pacemaker 200 is the same as the pulse generator 10 of the pacemaker 100.

The electrode line 40 includes a lead 42, an electrode 44, an interface 46, a ring electrode 48, and a fixing member 30.

Figure 11:
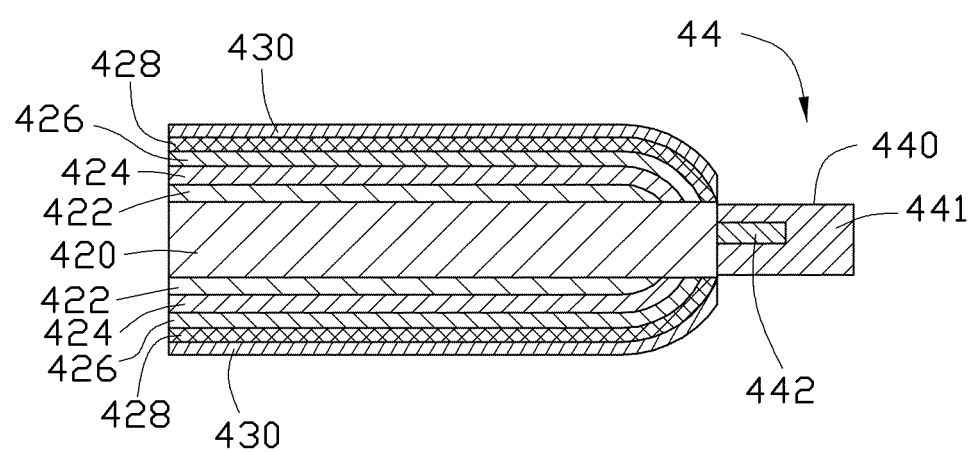
FIG. 11 shows a schematic structural view of another embodiment of an electrode line in the pacemaker of FIG. 10.

Referring to FIG. 11, the lead 42 includes a first conductor 420, a first insulation layer 422, a second conductor 424, a second insulation layer 426, a shielding layer 428, and a sheath 430 arranged from inside to outside.

The first conductor 420 is the same as the first conductor 222. A first end of the first conductor 420 is electrically connected to the interface 46. A second end of the first conductor 420 is electrically connected to the electrode 44, enabling the electrode 44 to be electrically connected to the pulse generator 10 through the first conductor 420 and the interface 46.

The first insulation layer 422 can be located on an outer surface of the first conductor 420. A material of the first insulation layer 422 can be polytetrafluoroethylene, polyethylene, polypropylene, polystyrene, polyethylene foam, and nano-clay-polymer composite material. In one embodiment, the insulation layer 422 is made of polyethylene foam.

The second conductor 424 can be located on an outer surface of the first insulation layer 422. The second conductor 424 can be a carbon nanotube wire or a metal wire. The carbon nanotube wire or the metal wire can wind along an axis of the first insulation layer 422 or parallel to an axis of the first insulation layer 422. In one embodiment, the second conductor 424 is a twisted carbon nanotube wire winding along the axis of the first insulation layer 422. A first end of the second conductor 424 is electrically connected to the interface 46, and a second end of the second conductor 424 is electrically connected to the ring electrode 48. Thus, the ring electrode 48 is electrically connected to the pulse generator 10 through the second conductor 424 and the interface 46.

The second insulation layer 426 can be located on an outer surface of the second conductor 424. A material of the second insulation layer 426 can be polytetrafluoroethylene, polyethylene, polypropylene, polystyrene, polyethylene foam, and nano-clay-polymer composite material.

The shielding layer 428 can be located on an outer surface of the second insulation layer 426 and can be used to shield electromagnetic signals or external signals. In one embodiment, the second insulation layer 426 is made of a drawn carbon nanotube film.

The sheath 430 can be located on an outer surface of the shielding layer 428 and can be used to prevent the lead 42 from machinery damage, chemical exposure damage, for example.

The electrode 44 can include a carbon nanotube composite structure. The carbon nanotube composite structure can be formed by at least one carbon nanotube structure 442 and a matrix 441. Each carbon nanotube structure 442 can have a first end and a second end opposite to the first end. The matrix 441 can have a first surface and a second surface 440 substantially perpendicular to the first surface. The at least one carbon nanotube structure 442 can be located in the matrix 441. Specifically, the first end of the at least one carbon nanotube structure 442 can be located in the matrix 441 and the at least one carbon nanotube structure 442 can be substantially parallel to the second surface 440 of the matrix 441. A distance between the at least one carbon nanotube structure 442 and the second surface 440 of the matrix 441 can be less than 10 micrometers. The second surface 440 of the matrix 441 can be used to contact and stimulate the brain tissue or the heart tissue. The second end of the at least one carbon nanotube structure 442 can protrude out of the first surface of the matrix 441 and can be electrically connected to the first conductor 420 by the conductive glue. The carbon nanotube composite structure can still have good conductivity if the distance between the at least one carbon nanotube structure 442 and the at least one second surface 440 of the matrix 441 is less than 10 micrometers. In one embodiment, the carbon nanotube composite structure includes a flocculated carbon nanotube film.

The ring electrode 48 can be located on an outer surface of the sheath 430 adjacent to the electrode 44. The ring electrode 48 can be a conductive coil and can be electrically connected to the second conductor 424. A material of the ring electrode 48 can be a metal or alloy having good conductivity. In one embodiment, the electrode 44 is made of platinum-iridium alloy.

In some embodiments, the shielding layer 428 is located on the outer surface of the first insulation layer 422, and the second conductor 424 is located on the outer surface of the second insulation layer 426. Thus, the shielding layer 428 can be used to shield the first insulation layer 422 from electromagnetic signals of the second conductor 424.

The fixing member 30 can be fixed on an outer surface of the sheath 430 adjacent to the electrode 44.

In use, the electrode line 40 is implanted into the tissue of the body, and the electrode 44 is fixed to contact a chosen tissue by the fixing member 30. A sensing signal can be obtained from the chosen tissue by the ring electrode 48 and transported to the pulse generator 10 by the second conductor 424. An electrical pulse signal can be generated by the pulse generator 10 according to the sensing signal and transported to the electrode 44 through the first conductor 420. The electrical pulse signal can stimulate and treat the chosen tissue.

The pacemaker has the following advantages. First, the electrode composed of carbon nanotubes and matrix has high strength and durability, thus increasing the durability of the pacemaker. Second, the carbon nanotubes in the electrode are oriented along a preferred orientation, so that the electrode has good conductivity. Third, an effective contact area between the electrode and the chosen tissue can be increased because of the large specific surface area of carbon nanotube, thus dramatically improving an efficiency of the pacemaker.

It is to be understood, however, that even though numerous characteristics and advantages of certain inventive embodiments have been set out in the foregoing description, together with details of the structures and functions of the embodiments, the disclosure is illustrative only; and that changes may be made in detail, especially in matters of arrangement of parts within the principles of the present disclosure to the full extent indicated by the broad general meaning of the terms in which the appended claims are expressed.

What is claimed is:

1. An electrode line for a pacemaker, the electrode line comprising a lead having an end and an electrode electrically connected to the end of the lead, the electrode comprising:
    a carbon nanotube composite structure comprising a matrix and a carbon nanotube structure located in the matrix, wherein the carbon nanotube structure comprises at least one carbon nanotube wire or at least one carbon nanotube film comprising a plurality of carbon nanotubes joined end to end;
    wherein the matrix comprises a first surface and a second surface substantially perpendicular to the first surface, the carbon nanotube structure has a first end and a second end opposite to the first end, the carbon nanotube structure is substantially parallel to the second surface of the matrix, a distance between the carbon nanotube structure and the second surface of the matrix is less than 10 micrometers, and the first end of the carbon nanotube structure protrudes out of the first surface of the matrix and is electrically connected to the end of the lead, the second end is buried in the matrix, an outer surface of the second end is entirely coated by the matrix, and the second surface of the matrix is conductive.

2. The electrode line of claim 1, wherein the distance between the carbon nanotube structure and the second surface of the matrix is less than 100 nanometers.

3. The electrode line of claim 1, wherein the distance between the carbon nanotube structure and the second surface of the matrix is in a range from about 20 nanometers to about 30 nanometers.

4. The electrode line of claim 1, wherein a material of the matrix is selected from the group consisting of epoxy resins, bismaleimide resins, cyanate ester resins, polypropylene, polyethylene, polystyrene, polyvinyl alcohol, polyphenylene enol, polycarbonate, and poly methyl methacrylate.

5. The electrode line of claim 1, the carbon nanotube composite structure comprises a plurality of carbon nanotube structures spaced from each other.

6. The electrode line of claim 1, wherein the at least one carbon nanotube wire or the at least one carbon nanotube film is substantially parallel to the second surface of the matrix.

7. The electrode line of claim 6, wherein the carbon nanotube structure comprises a plurality of carbon nanotube films stacked with each other, and each carbon nanotube film comprises the plurality of carbon nanotubes.

8. The electrode line of claim 7, wherein the plurality of carbon nanotubes in the carbon nanotube structure is oriented substantially along a same direction perpendicular to the first surface of the matrix.

9. The electrode line of claim 8, wherein the plurality of carbon nanotubes is joined by van der Waals force therebetween along an orientation direction of the plurality of carbon nanotubes.

10. The electrode line of claim 7, the plurality of carbon nanotubes in the carbon nanotube structure is entangled with each other.

11. The electrode line of claim 6, wherein the carbon nanotube structure comprises a plurality of carbon nanotube wires spaced from each other, the plurality of carbon nanotube wires is substantially perpendicular to the first surface of the matrix, each of carbon nanotube wires comprises a plurality of carbon nanotubes.

12. The electrode line of claim 11, wherein the plurality of carbon nanotubes in each carbon nanotube wire is substantially oriented along an axis of each carbon nanotube wire.

13. The electrode line of claim 12, wherein the plurality of carbon nanotubes is joined end to end by van der Waals force therebetween along the axis of each carbon nanotube wire.

14. The electrode line of claim 11, wherein the plurality of carbon nanotubes in each carbon nanotube wire is aligned helically around an axis of each carbon nanotube wire.

15. The electrode line of claim 1, wherein the carbon nanotube structure comprises a plurality of interspaces therein, and a portion of the matrix is located in the plurality of interspaces of the carbon nanotube structure.

16. A pacemaker, comprising:
an electrode line comprising a lead and an electrode electrically connected to an end of the lead, the electrode comprising:
a carbon nanotube composite structure comprising a matrix and a carbon nanotube structure located in the matrix, wherein the carbon nanotube structure comprises at least one carbon nanotube wire or at least one carbon nanotube film comprising a plurality of carbon nanotubes joined end to end;
wherein the matrix comprises a first surface and a second surface substantially perpendicular to the first surface, the carbon nanotube structure has a first end and a second end opposite to the first end, the carbon nanotube structure is substantially parallel to the second surface of the matrix, a distance between the carbon nanotube structure and the second surface of the matrix is less than 10 micrometers, and the first end of the carbon nanotube structure protrudes out of the first surface of the matrix and is electrically connected to the end of the lead, the second end is buried in the matrix, an outer surface of the second end is entirely coated by the matrix, and the second surface of the matrix is conductive.

17. The pacemaker of claim 16, wherein the lead comprises a first conductor electrically connected to the first end of the carbon nanotube structure.

18. The pacemaker of claim 17, wherein the electrode line further comprises a ring electrode and a second conductor electrically connected to the ring electrode.

19. The pacemaker of claim 14, wherein the plurality of carbon nanotubes is combined firmly by van der Waals attractive force therebetween to form a free-standing structure, a plurality of interspaces is defined by the adjacent carbon nanotubes in the carbon nanotube structure, and a part of the matrix is located in the plurality of interspaces of the carbon nanotube structure.

* * * * *